United States Patent [19]

Deya et al.

[11] Patent Number: 5,034,064
[45] Date of Patent: Jul. 23, 1991

[54] PRODUCTION PROCESS OF HIGH-PURITY LACTULOSE SYRUP

[75] Inventors: Eiki Deya, Saitama; Ken Takahashi, Hokkaido; Yoshihiro Ikeuchi, Saitama, all of Japan

[73] Assignee: Snow Brand Milk Products Co., Ltd., Hokkaido, Japan

[21] Appl. No.: 401,300

[22] Filed: Aug. 31, 1989

[30] Foreign Application Priority Data

Sep. 1, 1988 [JP] Japan .................. 63-216235

[51] Int. Cl.$^5$ .................................. C13K 5/00
[52] U.S. Cl. .................... 127/46.3; 127/46.2
[58] Field of Search ............... 127/46.2, 46.3, 46.1; 536/125, 127

[56] References Cited

U.S. PATENT DOCUMENTS 4,536,221  8/1985  Carobbi et al. .............. 127/46.2

OTHER PUBLICATIONS

Ion Exchangers: Properties and Applications, Konrad Dorfner, Ann Arbor Science Publishers Inc., 1973, p. 54.

*Primary Examiner*—Theodore Morris
*Assistant Examiner*—David M. Brunsman
*Attorney, Agent, or Firm*—Millen, White & Zelano

[57] ABSTRACT

A lactulose syrup suitable for use in the production of foods and drugs is produced by the alkali isomerization of lactose. Elimination of monosaccharides formed in the reaction mixture, such as galactose, is conducted by passing the reaction mixture through a column packed with beads of a strongly-acidic chromatographic cation-exchange resin, said beads having substantially the same crosslinking degree, and then collecting lactulose-containing eluate fractions. This process is suitable for the industrial production of a high-purity lactulose syrup.

11 Claims, 2 Drawing Sheets

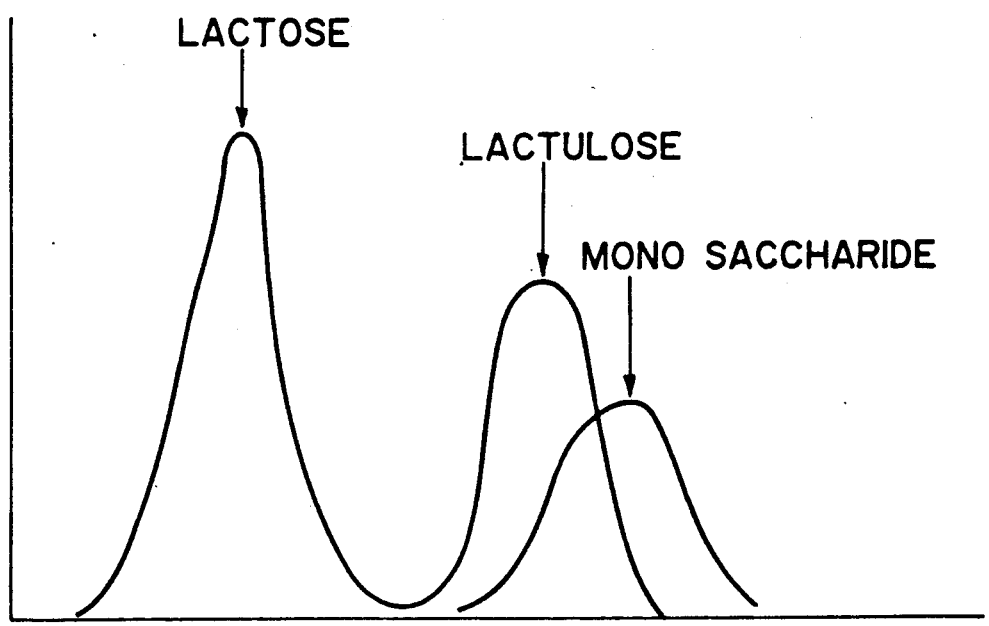
F I G. 1

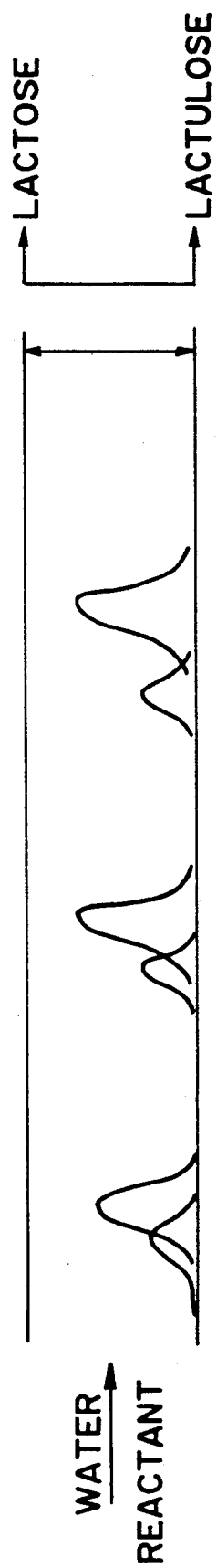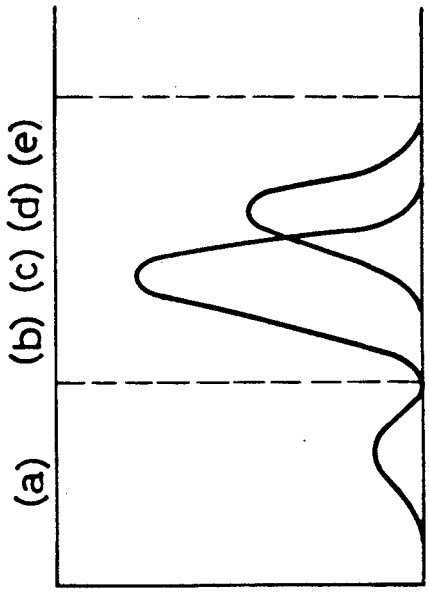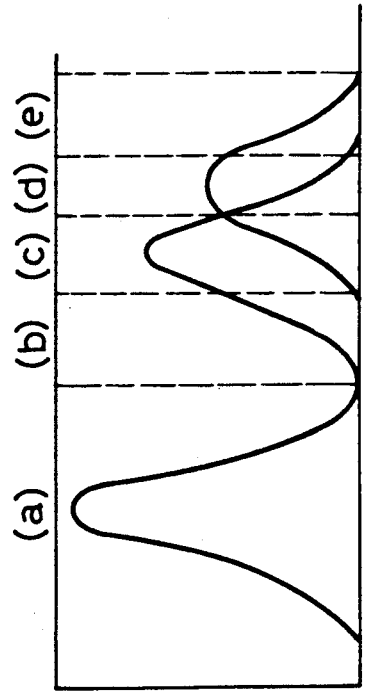

PRODUCTION PROCESS OF HIGH-PURITY LACTULOSE SYRUP

BACKGROUND OF THE INVENTION (1) Field of the Invention:

The present invention relates to a process for the production of a high-purity lactulose syrup on an industrial scale.

(2) Description of the Prior Art:

Lactulose is used as a bifidus growth factor in foods such as infant formulas and also as a senile constipation improver in drugs.

Regarding the production of lactulose, there are several known processes basis of the process in which lactulose is obtained by adding an alkalizing agent such as caustic soda, calcium hydroxide or caustic potassium to an aqueous solution of lactose and then heating the resultant mixture to effect isomerization of the lactose. Byproducts such as galactose are however formed in a large quantity if the lactose-based yield of lactulose is increased in these conventional processes. These conventional processes are therefore accompanied by the drawback that they require an additional step for the removal of such byproducts after the isomerization reaction. Although bromolysis and electrolysis are known methods for the elimination of these byproducts, they are both difficult to economically produce lactulose on an industrial scale.

It has therefore been attempted to minimize the formation of byproducts in the reaction. For example, Japanese Patent Publication No. 2984/1977 proposes a process for the production of lactulose in which in order to minimize the formation of monosaccharides—such as galactose—as byproducts, a solution of lactose is added with caustic soda in an amount of 0.27-0.53% based on the lactose, the resultant mixture is heated to a temperature of at least 70° C. to form lactulose, and removal of unreacted lactose by crystallization is repeated three times. In this process, the alkali isomerization reaction is however conducted under mild conditions to suppress the formation of monosaccharides—such as galactose—as byproducts, leading to a drawback that the yield of lactulose is as low as about 20% based on the weight of the initial lactose. It is another drawback that a great deal of time and labor is required for the removal of the unreacted lactose.

Namely, when the isomerization reaction of lactose into lactulose is conducted under mild conditions, the formation of monosaccharides such as galactose can be suppressed but the degree of isomerization is low. When the isomerization reaction is conducted under certain strong conditions, the degree of isomerization is increased but more byproducts such as monosaccharides are formed. Moreover, a subsequent complex purification step is indispensable for the production of high-purity lactulose whichever reaction conditions are employed. The above isomerization process was therefore not suited for practice on an industrial scale.

SUMMARY OF THE INVENTION

With the foregoing in view, the present inventors have conducted an extensive investigation to develop a process for producing lactulose on an industrial scale, in a good yield and at a low cost. As a result, it has been found that lactulose and monosaccharides such as galactose, said monosaccharides being byproducts, formed by the isomerization reaction can be easily separated from each other by means of beads of a strongly-acidic chromatographic cation-exchange resin, said beads having substantially the same crosslinking degree, leading to the completion of the present invention.

According to the present invention, the elimination of monosaccharides can be achieved with extreme ease. It is hence possible to conduct the isomerization reaction under conditions such that the yield of lactulose formed in the reaction mixture may become the highest in spite of the concurrent formation of monosaccharides during the isomerization reaction. Namely, byproducts are formed in a relatively high yield under the reaction conditions which allow the formation of lactulose in the highest yield. Therefore, it has conventionally been difficult to achieve a high overall yield for lactulose. However, the present invention has made it possible to efficiently recover lactulose, which has been formed in the reaction mixture, at a high level of purity by a simple procedure.

Moreover, if the strongly-acidic chromatographic cation-exchange resin is in alkaline earth metal type, e.g., the $Ca^{2+}$-salt from or $Mg^{2+}$-type, lactose-containing eluate fractions can continuously be collected by simply passing a lactulose-containing reaction mixture, which is obtained by the isomerization reaction of lactose, through a column packed with beads of the cation-exchange resin without separately removing lactose from the mixture in advance. The mechanism of this invention is basically attributable to the molecular sieve effect potentially exhibited by the strongly-acidic chromatographic cation-exchange resin, i.e., because of differences in molecular size, not molecular weight.

As a production process of a lactulose syrup which can enhance the above-mentioned effects further, the present invention provides a process for producing a high-purity lactulose syrup from lactose by adding an alkalizing agent to an aqueous solution of the lactose in order to conduct an isomerization reaction. The process comprises the following consecutive steps:

(a) passing the reaction mixture over an $H^+$-type cation-exchange resin, thereby removing the alkalizing agent and terminating the isomerization reaction;

(b) passing the resultant reaction mixture, from which, if necessary, lactose is removed by crystallization and filtration, through a column or columns packed with beads of a strongly-acidic chromatographic cation-exchange resin, said beads having substantially the same crosslinking degree, and collecting lactulose-containing eluate fractions; and (c) concentrating the lactulose-containing eluate fractions thus collected.

BRIEF DESCRIPTION OF THE DRAWINGS

FIG. 1 is a graph showing the elution patterns of lactose, lactulose and mono saccharide which are contained in the isomerization reaction mixture, upon chromatographing the reactor mixture once over the strongly-acidic chromatographic cation exchange resin which is of the alkaline earth metal type.

FIG. 2 is a graph showing the changes in elution patterns of lactose and lactulose throughout a column packed with the strongly-acidic chromatographic cation exchange resin used in FIG. 1, upon passing the isomerization reaction mixture once through the column.

FIG. 3 is a graph showing the fractions into which the elution patterns illustrated in FIG. 1 may be divided based on the contents therein.

FIG. 4 is a graph showing the elution patterns upon passing the reaction mixture used in FIG. 1 three times through the column used in FIG. 2.

In FIGS. 3 and 4, fractions (a), (b), (c), (d) and (e) indicate a lactose fraction, a mono saccharide-rich fraction and a mono saccharide fraction, respectively.

DETAILED DESCRIPTION OF THE PREFERRED EMBODIMENTS

As described above, in one aspect of the present invention, byproducts such as monosaccharides are separated from a lactulose-containing reaction mixture obtained by the isomerization reaction of lactose by using beads of a stronglY-acidic chromatographic cation-exchange resin, said beads having substantially the same crosslinking degree, so as to obtain a high-purity lactulose syrup. This process can be applied to conventional production processes of lactulose The yield of lactulose can be easily improved by simply incorporating the process of the present invention in the conventional processes. This invention is hereinafter be described on the basis of a process according to a working mode of this invention, which contains the process described above and is suitable for use in the production of a high-purity lactulose syrup.

The aqueous lactose solution subjected to the isomerization reaction is an aqueous solution of purified lactose (purity: 99% min.). Preferably, the concentration of lactose is from about 40 wt. % to about 60 wt. %. As the alkalizing agent to be added to the aqueous lactose solution, a conventional alkalizing agent such as caustic soda, calcium hydroxide or caustic potassium can be used. It may preferably be added in an amount of from about 1 wt. % to about 30 wt. % based on the lactose. If the concentration of the aqueous lactose solution is too low, the efficiency is lowered in the subsequent concentration step. If it is too high, the efficiency of the next step, i.e., the neutralization step is lowered. If the alkalizing agent is added in an unduly small amount, the isomerization reaction is allowed to proceed only at a low velocity, resulting in a low degree of lactose isomerization. On the other hand, any unduly large amount of the alkalizing agent causes the isomerization reaction to proceed too fast, resulting in the formation of more byproducts such as galactose and also in the formation of less lactulose. The isomerization reaction can be conducted preferably at about 60° C. or higher, at which the isomerization reaction is conducted sufficiently for about 30 minutes or longer. By this isomerization reaction, from about 12 wt. % to about 70 wt. % of the lactose can be isomerized into lactulose. Since the present invention allows to set the conditions for the isomerization reaction in such a way as yielding lactulose at a possible highest concentration in the reaction mixture, it is no longer required to determine the conditions in such a way that the formation of byproducts may be minimized.

The lactose-based yield of lactulose in the isomerization reaction varies depending on the lactose concentrations, the kind and amount of the alkalizing agent added, heating conditions, facilities employed, etc. It is thus preferable to conduct a preliminary test on the conditions for the isomerization reaction in a laboratory and then to conduct the reaction under conditions capable for affording lactulose in a highest yield.

Incidentally, caustic soda is preferred as the alkalizing agent.

Next, the termination of the reaction is effected by removing the alkalizing agent by passing the reaction mixture over the $H^+$-type cation-exchange resin. The cation-exchange resin is preferably of the $H^+$-type. An $H^+$-type cation-exchange resin can effectively catch $Na^+$, $Ca^{2+}$, $K^+$ and the like, which have higher selectivity than $H^+$. So long as such a neutralization reaction can be performed, the cation-exchange resin may be strongly acidic or weakly acidic. For example, "Amberlite IRC-50" (trade name; product of Rohm & Haas Co.) can be used. The neutralization reaction relying upon the cation-exchange resin does not induce unnecessary side reactions in the reaction solution so that byproducts are not formed and impurities are not mixed.

After the termination of the reaction, the reaction mixture is concentrated to a total solids content of at least about 70% and is then allowed to stand overnight at 25° C. to crystallize lactose. If the concentrate is left over at a temperature lower than 25° C., resulting crystals of lactose are small so that their removal is difficult. It is thus preferred to allow the concentrate to stand at 25° C. The lactose thus crystallized is then filtered off by a vacuum filter or the like. This crystallization and removal of lactose are repeated if necessary, whereby the content of lactose is lowered to from about 90 wt. % to about 3.9 wt. % based on the whole solids. The amount of lactose still remaining in the lactulose syrup as the final product is practically determined in this stage. Therefore, the crystallization and removal of lactose are conducted to a desired extent. The content of lactulose in the reaction solution from which lactose has been removed by filtration generally ranges from about 50 wt. % to about 80 wt. % based on the whole solids. The reaction mixture still contains monosaccharides such as galactose and colored substances at relatively high levels.

If the strongly-acidic chromatographic cation-exchange resin, which is used in the next step for separating lactulose from impurities, e.g., monosaccharides, is of the alkaline earth metal type, e.g., the $Ca^{2+}$-type or $Mg^{2+}$-type, the above-described step of crystallization and removal of lactose can be skipped because the cation-exchange resin exhibits a molecular sieve effect on lactose, as well as on monosacchararides and colored substances.

The resultant filtrate is next passed through a column packed with beads of a strongly-acidic chromatographic cation-exchange resin, said beads having substantially the same crosslinking degree, whereby lactulose is separated from byproducts such as monosaccharides and colored substances.

The term "strongly-acidic chromatographic cation-exchange resin" as used herein means a strongly-acidic cation-exchange resin useful in ion-exchange chromatography. This resin is formed of a copolymer resin of a compound having one or more ion-exchanging groups, such as sulfonic acid, and a polymerizable compound such as divinylbenzene or a base resin such as a styrene-divinylbenzene copolymer resin and ion-exchanging groups introduced in the copolymer resin. The crosslinking degree of the copolymer resin or the like, which constitute individual beads, falls within a specific range, so that the individual beads have similar porosities of network and physical properties and contain a predetermined constant number of ion-exchanging groups.

By the term "constant" as used herein is meant that the column may be regarded as homogeneous as a whole. The crosslinking degree may therefore range from about 0.4% to about 0.8%. A gel-type resin is preferred. It is preferable that individual beads are substantially in the same gel state and have similar ion-exchange capacity.

Use of an ion-exchange resin in which individual beads have similar physical properties and ion-exchange capacity and have a narrow bead size distribution makes it possible to narrow down the peak widths of impurities such as monosaccharides and colored substances in the reaction mixture, so that monosaccharides and colored substances can be removed efficiently.

Examples of the strongly-acidic cation-exchange resin usable in the present invention include those containing sulfonic groups as ion-exchanging groups, for instance, Amberlite CG-60 (trade name; product of Japan Organo Co., Ltd.). They may be either of the $H^+$ type or of the $Na^+$ type.

By passing the reaction mixture, from which lactose has been removed by filtration as described above if necessary, through a column or columns having a predetermined volume and packed with beads of a strongly-acidic cation-exchange resin, monosaccharides such as galactose can be separated from lactulose owing to the differences in molecular size. In this case, sufficient fractionation is infeasible unless the individual beads of the ion-exchange resin have substantially the same physical properties, namely, substantially the same crosslinking degree.

According to this invention, the strongly-acidic cation-exchange resin can also be of the alkaline earth metal type, e.g., the $Ca^{2+}$-type or $Mg^{2+}$-type. In this case, lactulose-containing eluate fractions can continuously be collected by simply passing the reaction mixture through a column or columns packed with beads of the resin without separately removing lactose from the mixture in advance. The alkaline earth metal type may be prepared by bringing an $H^+$-type or an $Na^+$-type in contact with alkaline earth metal ions to convert the $H^+$-type or the $Na^+$-type into said alkaline earth metal type, or by regenerating a used $H^+$-type or a used $Na^+$-type using an alkaline earth metal salt solution as a regenerant, whereby the degree of swelling of the cation-exchange resin goes down, so that the network size of the resin becomes larger accordingly. As a result, the alkaline earth metal type can preferentially catch lactose as well as other impurities, rather than lactulose, because of differences in molecular size, even though lactose has the same molecular weight as lactulose does. The network size of the resin, which is related to the molecular sieve effect, is based, first, on the degree of crosslinking and, second, on the degree of swelling.

In a case using the alkaline earth metal type resin, since an affinity of the alkaline earth metal with a sugar causes effects on chromatographic absorption, the difference in affinity between with lactose (M.W. 342) and with lactulose (M.W. 342) leads to their separation although both in common with a disaccharide group.

In other words, in a case using the alkaline earth metal type strongly-acidic cation exchange resin, lactose is separated from lactulose by both molecular sieve and ionic affinity effects.

The lactulose-containing eluate fractions are substantially the same as lactose-containing eluate fractions if an $H^+$-type or an $Na^+$-type is used. However, eluate fractions of mono-saccharides are generally obtained after the above-mentioned fractions. Collection of the lactulose-containing eluate fractions hence leads to separation of the monosaccharides and also to simultaneous capture of colored substances. Upon ion-exchange, it is necessary to optimize the amount of the resin to be packed in the column and the amount of the reaction mixture to be charged into the column. They have to be adjusted suitably depending on the kind, bead size and properties of the ion-exchange resin, the shape of the column, etc., so that lactulose-containing fractions can be collected efficiently. For example, based on the volume of the column packed with the ion-exchange resin, the reaction mixture may be passed at a flow rate of about 20%/hr of the column volume. The content of lactulose in the lactulose-containing fractions collected reaches close to 90 wt. % of the whole solids, so that monosaccharides and other byproducts can be removed almost completely.

Next, the fractions collected above are concentrated to a desired extent so that a high-purity lactulose syrup is obtained. By the above procedures, the yield of lactulose based on the lactose as the starting material can be increased to from about 10% to about 90%. In addition to the steps described above, this invention may additionally comprises centrifugation and/or addition of ethanol upon crystallization and removal of lactose, and/or pH adjustment upon passing the reaction mixture through the column as needed, thereby making it possible to increase the purity of lactulose further. In addition, the lactulose-containing eluate fractions may be concentrated and then dried to obtain lactulose in the form of powder.

This invention will hereinafter be described specifically by the following examples.

EXAMPLE 1

Warm water (600 kg) was added to 400 kg of commercially-available purified lactose (purity: 99%) to dissolve the latter. The resultant solution was added with 40 kg of caustic soda and then heated at 80° C. for 30 minutes to conduct an alkali isomerization reaction. The reaction mixture was passed over 150 l of a cation-exchange resin to remove caustic soda, thereby terminating the reaction.

After the termination of the reaction, the reaction mixture had the following saccharide composition: 15.2 wt. % of lactose, 53.1 wt. % of lactulose and 31.7 wt. % of galactose, all based on the whole solids. Thereafter, the reaction mixture was concentrated to a total solids content of 70% in a concentrator manufactured by Wiegand Inc. The resultant concentrate was allowed to stand overnight at 25° C. Lactose thus crystallized was filtered off by a vacuum filter.

The filtrate had the following saccharide composition: 5.1 wt. % of lactose, 59 wt. % of lactulose and 35.2 wt. % of galactose, all based on the whole solids. The filtrate was then subjected to chromatography through a column having a diameter of 2 m and a length of 10 m and packed with "CG-60 Cation-Exchange Resin ($Na^+$-Type)" (trade name; product of Japan Organo Co., Ltd.).

The strongly-acidic cation-exchange resin was composed of a copolymer of styrene and divinylbenzene and contained sulfonic groups as ion-exchanging groups. The beads had a particle size in a range of from 0.2 mm to 0.4 mm and substantially the same crosslinking degree (about 0.6%). It was of the gel type.

The filtrate was passed at 6,200 l/hr. Upon an elapsed time of 118 minutes after the initiation of charging, collection of eluate was started as lactulose-containing fractions. About 6,090 l was collected (peak: 136 minutes from the initiation of charging). Incidentally, fractions containing monosaccharides such as galactose began to occur about 160 minutes after the initiation of charging. Further, colored substances and the like were substantially captured on the ion-exchange resin.

The thus-eluted lactulose-containing fractions were concentrated to prepare a syrup whose water content was 30%. The syrup prepared as described above had the following saccharide composition: 89.2 wt. % of lactulose and 8.3 wt. % of lactose, both based on the whole solids. The solid weight of lactulose was 203.6 kg, and its yield was 50.9% based on the starting lactose.

EXAMPLE 2

A lactulose syrup was prepared in a manner similar to Example 1 except that the chromatography was practiced using XT-1007 (product of Tokyo Organic Chemical Industry Co., Ltd.) (crosslinking degree: 0.6%) as an ion-exchange resin. The peak of lactulose-containing fractions occurred about 123 minutes after the initiation of charging, while the peak of fractions containing monosaccharides such as galactose appeared about 167 minutes after the initiation of charging. The lactulose-containing fractions were collected and concentrated into a syrup, which had the following saccharide composition: 94.3 wt. % of lactulose and 4.2 wt. % of lactose, both based on the whole solids. The solid weight of lactulose was 201.5 kg, and its yield was 50.4% based on the starting lactose.

EXAMPLE 3

Two columns, each having a diameter of 5.8 cm and a length of 5 m, were packed with the CG-60 Cation-Exchange Resin ($Na^+$-type) used in Example 1. By passing 3 l/l-resin of a 1N calcium chloride solution through the columns, the resin was regenerated as a $Ca^{2+}$-type.

A reaction mixture having the saccharide composition: 79.6 wt. % of lactose, 18.3 wt. % of lactulose and 2.1 wt. % of galactose, which was obtained in the same manner as in Example 1, was directly passed through the columns packed with the regenerated resin so as to obtain the lactulose-containing syrup. The thus-obtained syrup had the following saccharide composition: 90.8 wt. % of lactulose, 0.6 wt. % of lactose and 8.6 wt. % of monosaccharides.

Although the invention has been described with preferred embodiments, it is to be understood that variations and modifications may be resorted to as will be apparent to those skilled in the art. Such variations and modifications are to be considered within the purview and the scope of the claims appended hereto.

We claim:

1. In a process for the production of a lactulose syrup, wherein lactose is alkali isomerized to produce an aqueous alkaline lactose-containing solution from which the alkali is removed with a cation exchange resin and the solution is thereafter concentrated to produce the lactulose syrup, the improvement wherein prior to the concentration thereof, the lactulose-containing solution from which the alkali has been removed is passed through a chromatographic column of physically and chemically substantially uniform beads of the salt form of a strongly acidic cation-exchange resin, and the lactulose-containing fraction of the solution is fractionally eluted from the column.

2. The process of claim 1, therein the isomerization reaction is conducted by mixing a 40–60 wt. % aqueous solution of lactose with caustic soda in an amount of 1–30 wt. % of the lactose and then heating the resultant mixture at a temperature of at least 60° C.

3. The process of claim 1, wherein the starting lactulose-containing solution is one from which lactose has been removed.

4. The process of claim 1, wherein the salt of the chromatographic cation-exchange resin is an alkaline earth metal salt.

5. The process of claim 1, wherein the starting lactulose solution contains the lactose remaining after the alkali isomerization reaction.

6. The process of claim 1, wherein the salt of the chromatographic cation-exchange resin is an alkaline earth salt.

7. The process of claim 1, wherein the cationic exchange resin is a copolymer of styrene and divinylbenzene whose ion-exchange groups are sulfonic acid groups.

8. The process of claim 7, wherein starting lactulose-containing solution is one from which lactose has been removed and wherein the salt of the chromatographic cation-exchange resin is an alkaline earth metal salt.

9. The process of claim 8, wherein the salt is the sodium salt.

10. The process of claim 6, wherein the starting lactulose solution contains the lactose remaining after the alkali isomerization reaction and wherein the salt of the chromatographic cation-exchange resin is an alkaline earth salt.

11. The process of claim 7, wherein the salt is the calcium salt.

* * * * *

UNITED STATES PATENT AND TRADEMARK OFFICE
CERTIFICATE OF CORRECTION

PATENT NO. : 5,034,064
DATED : 07/23/91
INVENTOR(S) : Eiki DEYA et al.

It is certified that error appears in the above-identified patent and that said Letters Patent is hereby corrected as shown below:

ON THE TITLE PAGE: " IN THE HEADING" ------

The Assignee is listed as

SNOW BRAND PRODUCTS CO., LtD.

should read - - - - - - -

Assignee: AULT FOODS LIMITED
A CANADIAN CORPORATION
405 THE WEST MALL
ETOBICOKE, ONTARIO, CANADA Col. 8, CLAIM: 1   LINE: 3   Reads - - lactose-containing should read - - lactulose-containing Signed and Sealed this Fifteenth Day of December, 1992

*Attest:*

DOUGLAS B. COMER

*Attesting Officer*    *Acting Commissioner of Patents and Trademarks*